United States Patent [19]

Suzuki et al.

[11] Patent Number: 5,073,385

[45] Date of Patent: Dec. 17, 1991

[54] BOEHMITE-TYPE ALUMINUM HYDROXIDE, PROCESS FOR PREPARING SAME AND PHOSPHATE ION ADSORBENT CONTAINING SAME AS EFFECTIVE COMPONENT

[75] Inventors: Takeshi Suzuki, Tokushima; Mineaki Kabayama, Naruto, both of Japan

[73] Assignee: Tomita Pharmaceutical Co., Ltd., Tokushima, Japan

[21] Appl. No.: 434,177

[22] Filed: Nov. 13, 1989

[30] Foreign Application Priority Data

Nov. 14. 1988 [JP] Japan ................................ 63-288592

[51] Int. Cl.$^5$ ............................................. A01N 59/06
[52] U.S. Cl. .................................... 424/690; 424/691; 514/819
[58] Field of Search ................. 424/682, 688, 690, 696

[56] References Cited

U.S. PATENT DOCUMENTS

| | | | |
|---|---|---|---|
| 3,226,188 | 12/1965 | Rüter et al. | 423/111 |
| 3,395,221 | 7/1968 | Snyder et al. | 424/690 |
| 3,518,064 | 6/1970 | Lewin | 424/690 |
| 4,098,883 | 7/1978 | Madaus et al. | 424/690 |
| 4,332,778 | 6/1982 | Hobday | 423/123 |
| 4,514,389 | 4/1985 | Miyata | 424/688 |
| 4,542,019 | 9/1985 | Lezdey | 424/690 |
| 4,576,819 | 3/1986 | Miyata | 424/688 |
| 4,639,362 | 1/1987 | Schanz | 424/690 |
| 4,814,106 | 3/1989 | Kvant | 252/363.5 |
| 4,915,957 | 4/1990 | Schneider et al. | 424/690 |

OTHER PUBLICATIONS

Chemical Abstracts, vol. 98, 200726(b)–Gunnarsson–1983.

*Primary Examiner*—Frederick E. Waddell
*Assistant Examiner*—T. J. Criares
*Attorney, Agent, or Firm*—Larson and Taylor

[57] ABSTRACT

Discosed are (i) a boehmite-type aluminum hydroxide which is represented by the formula $$AlO(OH) \cdot xSO_4 \cdot nH_2O$$

wherein $0.01 < x < 0.10$ and $0 \leq n < 1$; and (ii) a process for preparing a boehmite-type aluminum hydroxide represented by the formula $$AlO(OH) \cdot xSO_4 \cdot nH_2O$$

wherein $0.01 < x < 0.10$ and $0 \leq n < 1$, the process comprising surface-treating a boehmite-type aluminum hydroxide with sulfuric acid or a sulfate capable of forming sulfuric acid by heating or by hydrolysis, the boehmite-type aluminum hydroxide to be treated being represented by the formula $$AlO(OH) \cdot mH_2O$$

wherein $0 \leq m < 1$.

14 Claims, 3 Drawing Sheets

BOEHMITE-TYPE ALUMINUM HYDROXIDE, PROCESS FOR PREPARING SAME AND PHOSPHATE ION ADSORBENT CONTAINING SAME AS EFFECTIVE COMPONENT

FIELD OF THE INVENTION

This invention relates to a boehmite-type aluminum hydroxide, a process for preparing the same and a phosphate ion adsorbent containing the same as its effective component.

PRIOR ART

A phosphate ion binder chemically binds to the phosphate inons delivered to intestines by the food containing the phosphoric acid components, preventing the absorption of the phosphate ions in the body. With this activity, the phosphate ion binder is orally administered chiefly to patients with, e.g., hyperphosphatemia accompanying renal insufficiency. Dried aluminum hydroxide gels have been heretofore used as orally administrable phosphate ion binders. However, when a dried aluminum hydroxide gel is administered over a long period, a large amount of Al ions is accumulated in the human body and causes dialysis encephalopathy, aluminum poisoning or the like. Further the gel is not fully satisfactory in phosphate ion-adsorbing capacity.

In view of this problem, calcium carbonate agents are currently used in place of dried aluminum hydroxide gels. However, the calcium carbonate agents have a lower phosphate ion-adsorbing capacity than dried aluminum hydroxide gels and are also prone to decomposition due to the gastric acid or the like which leads to production of a large amount of Ca ions liable to induce hypercalcemia.

Other various binders and adsorbents are available but have the problems of safety hazards to the human body and low phosphate ion-adsorbing capacity.

DISCLOSURE OF THE INVENTION

Figure 1:
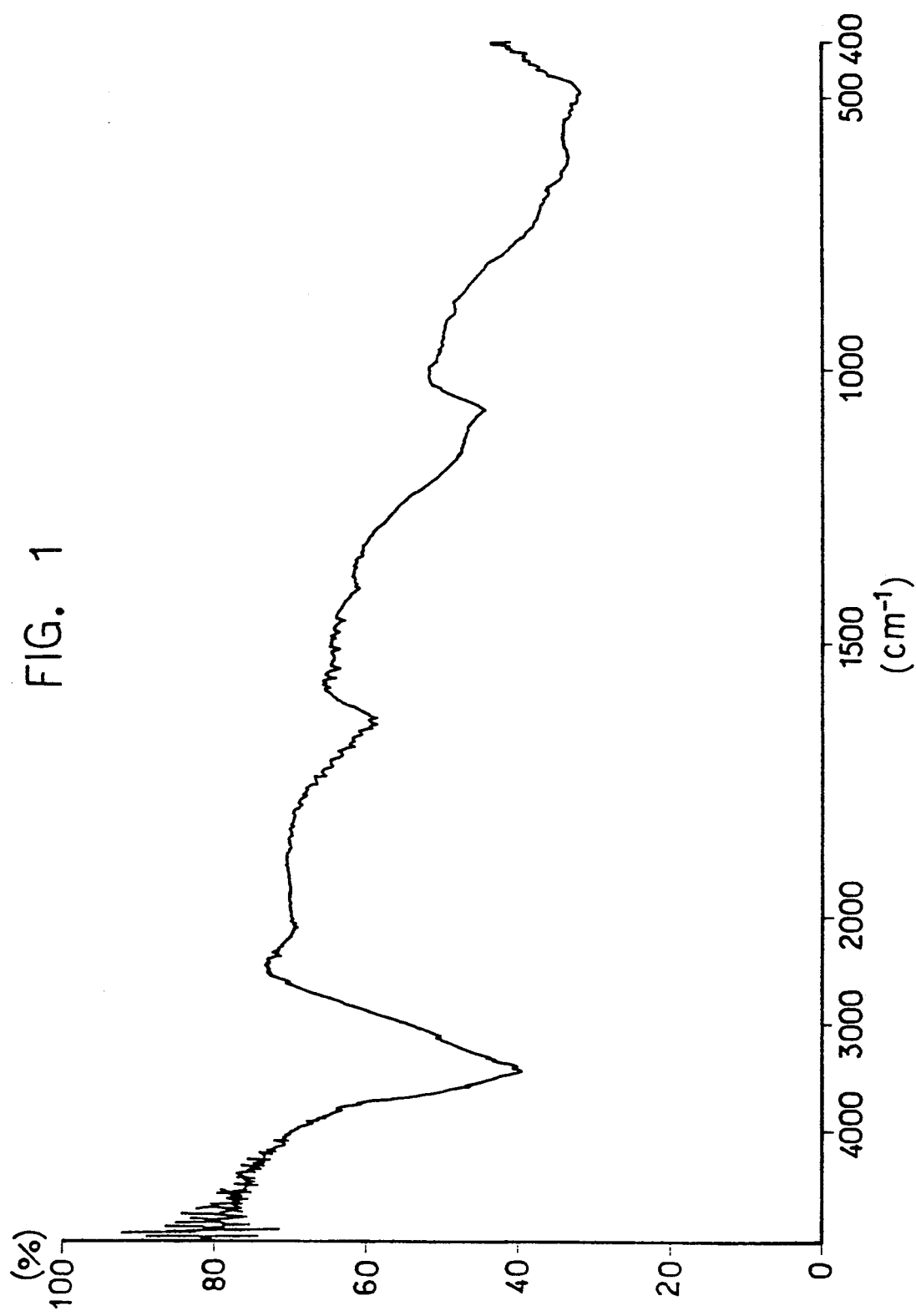
FIG. 1 shows the IR spectrum of the boehmite (I) of the invention prepared in Example 1.

It is an object of the invention to provide a boehmite-type aluminum hydroxide which even when administered for a long term is unlikely to accumulate Al ions in the human body, thus without causing dialysis encephalopathy, aluminum poisoning or the like.

It is another object of the present invention to provide a boehmite-type aluminum hydroxide having an outstanding phosphate ion-adsorbing capacity.

It is a further object of the invention to provide a process for preparing the boehmite-type aluminum hydroxide having the foregoing desirable properties.

It is a still further object of the invention to provide a phosphate-ion adsorbing agent containing as its effective component the boehmite-type aluminum hydroxide having the foregoing desirable properties.

Other objects and features of the present invention will become apparent from the following description.

According to the invention, there are provided a boehmite-type aluminum hydroxide which is represented by the formula $$AlO(OH) \cdot xSO_4 \cdot nH_2O \tag{1}$$

wherein $0.01 < x < 0.10$ and $0 \leq n < 1$, a process for preparing the boehmite-type aluminum hydroxide of the formula (1) and a phosphate ion-adsorbing agent containing as its effective component the aluminum hydroxide of the formula (1).

We conducted extensive research and found that when surface-treated with sulfuric acid, a boehmite-type aluminum hydroxide is given a specific amount of sulfate ions and imparted an outstanding phosphate ion-adsorbing capacity, namely about 5 to about 20 times as high as that of conventional phosphate-ion binders. Such aluminum hydroxide is not prone to decomposition due to the gastric acid as well as the alkaline liquid in intestines and are therefore unlikely to accumulate Al ions in the human body during a long-term administration, thus without causing dialysis encephalopathy, aluminum poisoning or the like. The present invention has been accomplished based on this novel finding.

Among the boehmite-type aluminum hydroxides of the formula (1) according to the present invention (hereinafter referred to as "present boehmite"), preferable are those in which $0.03 \leq x < 0.10$ and/or $0.2 \leq n \leq 0.8$ in view of the adsorption amount of phosphate ions.

The present boehmite has an outstanding phosphate ion-adsorbing capacity presumably for the following reason. A boehmite-type aluminum hydroxide for use as a starting material for forming the present boehmite (hereinafter referred to as "starting boehmite") has a phosphate ion-adsorbing capacity and contains two kinds of OH groups attached to Al ions, namely OH groups having a phosphate ion-adsorbing capacity and easily neutralizable with an acid (active OH groups) and OH groups having no phosphate ion-adsorbing capacity and neutralizable with an acid (semi-active OH groups). The starting boehmite contains a large quantity of semi-active OH group relative to active OH group.

When sulfuric acid is caused to act on the starting boehmite, the active OH groups and semi-active OH groups attached to the Al ions are removed on neutralization with hydrogen ions while the sulfate ions form a coordinate bond with the two Al ions, becoming sulfuric acid groups. The sulfuric acid groups bonded are stable and free of tendency to induce hydrolysis and are unlikely to dissociate on boiling. These sulfuric acid groups have the property of readily inducing replacement reaction with phosphate ions. Consequently the present boehmite obtained by treating the starting boehmite with sulfuric acid shows significant increase in phosphate ion-adsorbing capacity.

The present boehmite is a novel one having a specific amount of sulfuric acid groups and can be prepared by surface-treating the starting boehmite with sulfuric acid or a salt of sulfuric acid capable of producing sulfuric acid by heating or by hydrolysis (said salt of sulfuric acid will be hereinafter referred to merely as "sulfate" unless otherwise indicated).

Useful starting boehmites include, for example, a conventional boehmite-type aluminum hydroxide represented by the formula $$AlO(OH) \cdot mH_2O \quad (2)$$

wherein $0 \leq m < 1$. While suitably determinable without specific limitation, the particle size of starting boehmite is usually in tha range of about 1 to about 200 μm, preferably about 5 to about 15 μm.

The surface treatment can be carried out by bringing sulfuric acid or a sulfate into contact with the starting boehmite, for example, by adding dropwise an aqueous solution of sulfuric acid or an aqueous solution of a sulfate to an aqueous suspension of the starting boehmite with, when required, stirring.

The starting boehmite concentration in the aqueous suspension although not specifically limited usually ranges from about 5 to about 30% by weight, preferably about 10 to about 20% by weight.

The amount of an aqueous solution of sulfuric acid to be added for surface treatment is not specifically limitative but is in such range that the aqueous suspension of starting boehmite has a pH of about 1 to about 6, preferably about 1.5 to about 3.0. The sulfuric acid concentration in the aqueous solution of sulfuric acid is not critical, yet generally ranging from about 5 to about 10 w/v % to achieve a proper treatment. The surface treatment with an aqueous solution of sulfuric acid is conducted at a temperature of about 10° to about 60° C., preferably about room temperature. The treating time is not specifically limited, yet ranges from about 0.5 to about 3 hours, preferably about 1 to about 2 hours.

The amount of a sulfate to be added for surface treatment is about 1 to about 20 g, preferably about 5 to about 15 g, calculated as sulfate ions, per 100 g of the starting boehmite. Conventional sulfates can be used without specific limitation as a sulfate capable of producing sulfuric acid on heating. For example, ammonium sulfate and the like are desirable. As a sulfate capable of giving sulfuric acid by hydrolysis, conventional sulfates can be used without specific limitation. Among them, preferable are ammonium hydrogensulfate, sodium hydrogensulfate and potassium hydrogensulfate. The treating temperature in this case is in a range which permits the formation of sulfuric acid from the sulfate used. In other words, the treating temperature may be properly determined depending on the kind of sulfate used. For example, the treating temperature employed in using a sulfate capable of forming sulfuric acid by heating is in the range of about 80° to about 120° C., preferably about 90° to about 100° C., whereas the treating temperature in using a sulfate capable of forming sulfuric acid by hydrolysis ranges from about 20° to about 40° C., preferably about 25° to about 30° C. The treating time is not specifically limited in either case but is usually about 0.5 to about 2 hours, preferably about 1 to about 2 hours.

The present boehmite can be prepared by purifying the reaction mixture by conventional purification means after the surface treatment. For example, the residue (present boehmite) in the reaction mixture is filtered off, washed with water and dried at about 80° to about 90° C., followed, if necessary, by breaking. Use of an aqueous solution of sulfuric acid gives the present boehmite having a phosphate ion-adsorbing capacity of about 60 to about 70 mgPO$_4$/mg, and use of an aqueous solution of a sulfate provides the present boehmite having a phosphate ion-adsorbing capacity of about 35 to about 50 mgPO$_4$/mg.

The present boehmite may be used after adjustment to the desired particle size.

The present boehmite may be used itself as a phosphate ion-adsorbing agent or may be mixed with a diluent or a excipient commonly employed in the art such as fillers, extenders, binders, wetting agents, disintegrators, surfactants, lubricants, etc. to make the mixture into a preparation of specific form. While the form of preparation is not critical, granules and tablets are preferred.

The preparation of the invention is usually orally administered. The dose of the preparation to be administered is not specifically limited and can be suitably determined over a wide range. Yet the preparation of the invention is administered at a daily dose of about 3 to about 6 g calculated as the effective component per adult or may be given in 3 or 4 divided doses per day.

The present invention will be described below in greater detail with reference to the following Examples and Comparison Examples.

EXAMPLE 1

A 260 kg quantity of a starting boehmite (m=0.50) was added to 800 l of water and the mixture was stirred for 30 minutes to obtain a suspension with a pH of 7.5. To the suspension was added dropwise with stirring 260 l of an aqueous solution of sulfuric acid (10 w/v %) to give a reaction mixture having a pH of 1.8. The reaction mixture was stirred for 1 hour and the residue was filtered off, washed with water and dried at 90° C., giving a boehmite (I) according to the invention. Table 1 below shows the properties of the boehmite (I).

Figure 2:
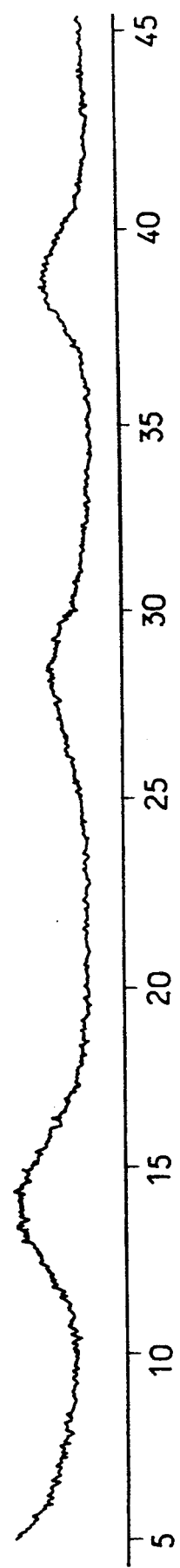
FIG. 2 shows the X-ray diffraction result of boehmite (I)

FIG. 1 shows the IR spectrum of the boehmite (I), and FIG. 2 shows the X-ray diffraction result of the boehmite (I). In FIG. 1, the peaks at 1000 to 1200 cm$^{-1}$ and at about 500 cm$^{-1}$ indicate the presence of sulfuric acid groups. The low peak at about 3100 cm$^{-1}$ is presumably derived from OH groups. The peak at about 3450 cm$^{-1}$ shows the presence of OH groups, and the peak at about 1650 cm$^{-1}$ the presence of H$_2$O molecules. FIG. 2 reveals that boehmite (I) has a structure peculiar to boehmites. Consequently, it is clear that no structural change occurred in the boehmite by treatment with sulfuric acid.

COMPARISON EXAMPLE 1

A boehmite (a) treated with hydrochloric acid was obtained by conducting the same procedure as in Example 1 with the exception of adding 20 l of 2N hydrochloric acid in place of 260 l of the aqueous solution of sulfuric acid (10 w/v %) (the final mixture had a pH of 5.0).

A boehmite (b) treated with nitric acid was prepared by effecting the same procedure as in Example 1 with the exception of adding 21.5 l of 2N nitric acid in lieu of 260 l of the aqueous solution of sulfuric acid (10 w/v %) (the final mixture had a pH of 5.0).

When the suspension with a pH of 5.0 or less was given with addition of 2N hydrochloric acid or 2N nitric acid, in either case the boehmite decomposed and the suspension became gelatinous. Consequently treatment was impossible in case of the suspension 5.0 or less in pH.

Table 1 shows the analysis results of boehmites (I), (a) and (b) prepared in Example 1 and Comparison Example 1 and the results of the test for phosphate ion-adsorbing capacity.

TEST FOR PHOSPHATE ION-ADSORBING CAPACITY

A 0.1 g portion of each boehmite was added to 100 ml of a 0.01% aqueous solution of disoldium phosphate and the mixture was stirred at 37°±2° C. for 1 hour. After cooling, the solids were filtered off with a glass filter. To 10 ml of the filtrate were added 2 ml of 10% sulfuric acid and 1 ml of a solution of ammonium molybdate (5 w/v %). The mixture was stirred for 5 minutes. The absorbance (equilibrium concentration, hereinafter referred to as "EC", unit: %) at 389 nm was measured by a spectrophotometer. The same procedure was conducted using a blank. The blank concentration (hereinafter referred to as "BC", unit: %) was obtained on the basis of the absorbance measured according to the specified calibration line. The adsorption amount was calculated by the following equation.

Adsorption amount (mg PO$_4$/mg) = $(BC - EC) \times 100 \times (95/142) \times (1000/100) \times (1/0.1)$

COMPARISON EXAMPLE 2

A boehmite (c) was prepared by performing the same procedure as in Example 2 with the exception of addition of a solution of about 6.6 g of sodium sulfate (about 4.5 g calculated as SO$_4$) in 60 ml of water in place of the solution of 6.2 g of ammonium sulfate in 40 ml of water (the final mixture had a pH of 5.0). Table 2 below shows the analysis result of the boehmite (c).

TABLE 2

|  | Example 2 (II) | Comp. Ex. 2 (c) |
|---|---|---|
| Al$_2$O$_3$ (%) | 69.11 | 69.95 |
| SO$_4$ (%) | 4.51 | 1.50 |
| Adsorption amount of phosphate ions (mg PO$_4$/g) | 37.21 | 19.52 |
| SO$_4$/Al$_2$O$_3$ (molar ratio) | 0.070 | 0.023 |
| 1:x:n (Note 1) | 1:0.035:0.29 | 1:0.011:0.40 |

(Note 1): AlO(OH).xSO$_4$.nH$_2$O

TABLE 3

| Final mixture (pH) | (Not treated) | 5.0 | 4.0 | 3.0 | 1.9 |
|---|---|---|---|---|---|
| Amount of aqueous solution of sulfuric acid (ml) | — | 30 | 60 | 80 | 125 |
| Al$_2$O$_3$ (%) | 68.27 | 67.90 | 65.76 | 65.84 | 65.00 |
| SO$_4$ (%) | 1.00*[2] | 4.16 | 4.98 | 7.49 | 8.32 |
| Adsorption amount of phosphate ions (mg PO$_4$/g) | 25.12 | 43.97 | 54.28 | 60.45 | 65.16 |
| SO$_4$/Al$_2$O$_3$ (molar ratio) | 0.016 | 0.065 | 0.080 | 0.121 | 0.136 |
| 1:x:n*[1] | 1:0.007:0.322 | 1:0.03:0.27 | 1:0.038:0.328 | 1:0.058:0.216 | 1:0.063:0.171 |

*[1]AlO(OH).xSO$_4$.nH$_2$o
*[2]The starting boehmite contains a small quantity of SO$_4$ as impurity.

Table 1 reveals that the boehmite (I) of the invention was about 3 times as high as phosphate ion-adsorbing capacity as the starting boehmite, whereas the comparative boehmites (a) and (b) achieved little improvement in this property. Table 1 also displays that the boehmite (I) of the invention was markedly superior in phosphate ion-adsorbing capacity to known phosphate ion-adsorbing agents such as dried aluminum hydroxide gel (9.4 mgPO$_4$/g), calcium carbonate (3.3 mgPO$_4$/g) and the like.

EXAMPLE 2

A 50 g quantity of a starting boehmite (m=0.50) was added to 350 ml of water and the mixture was stirred for 30 minutes to obtain a suspension with a pH of 7.2. To the suspension was gradually added with stirring a solution of 6.2 g of ammonium sulfate (4.5 g calculated as SO$_4$) in 40 ml of water to obtain a reaction mixture with a pH of 8.2. The reaction mixture was stirred at a temperature of 96° to 100° C. for 1 hour to give a reaction mixture having a pH of 7.2. The residue was filtered off, washed with water and dried at 90° C., giving a boehmite (II) according to the invention. Table 2 below shows the analysis result of the boehmite (II).

EXAMPLE 3

A 200 g quantity of a starting boehmite (m=0.32) was added to 1500 ml of water and the mixture was stirred to obtain a suspension having a temperature of 20° C. and a pH of 8.7. To the suspension was gradually added with stirring an aqueous solution of sulfuric acid (10 w/v %) in the amount as listed in Table 3 to give a suspension. In this way, suspensions 5.0, 4.0, 3.0 and 1.9, respectively in pH were prepared. Each suspension was further stirred for 30 minutes and the residue was filtered off, washed with water and allowed to stand at 60° C. overnight for drying, giving boehmites (III) to (VI) according to the invention. Table 3 below shows the analysis results of these boehmites.

Figure 3:
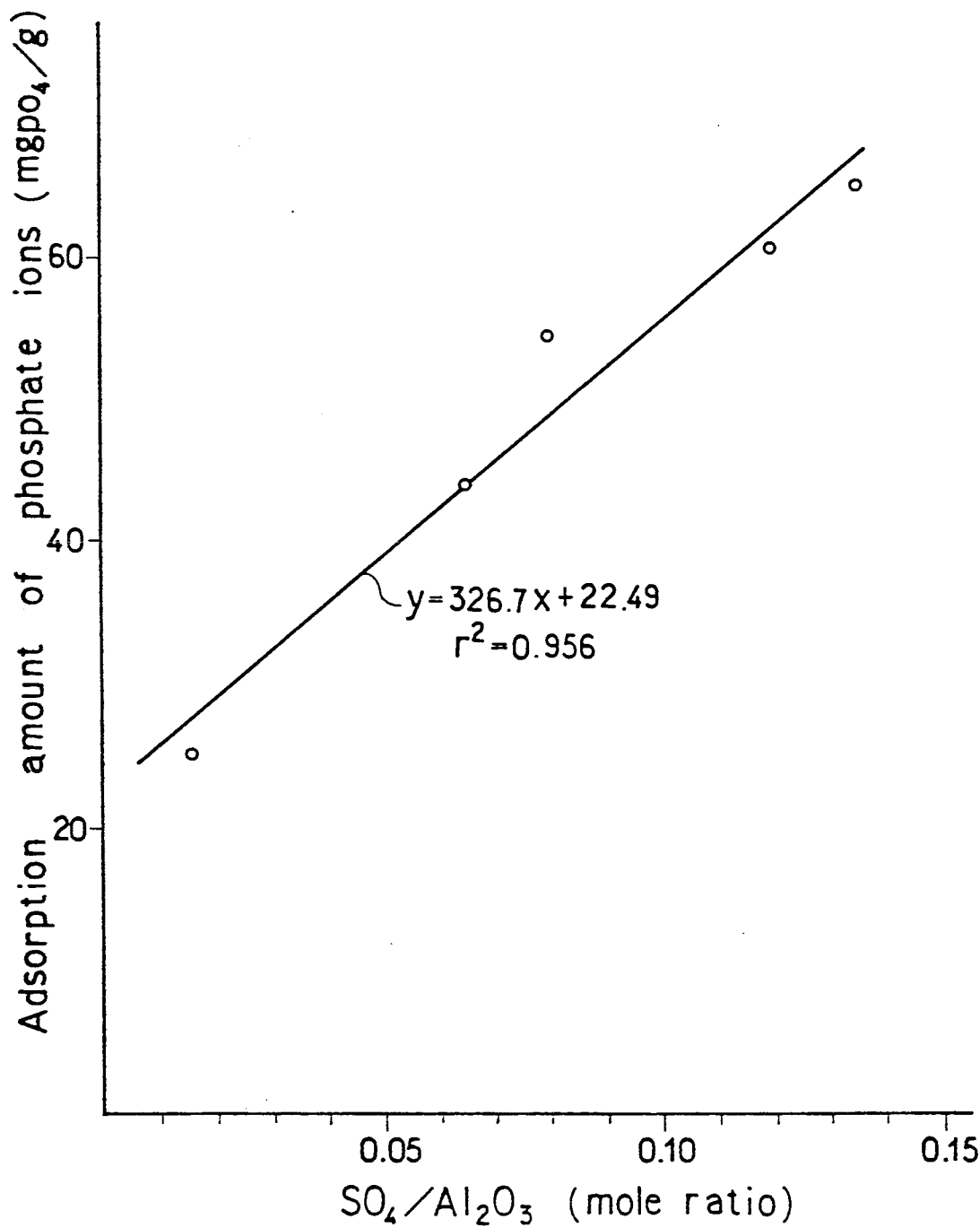
FIG. 3 shows the relationship between the ratio of $SO_4/Al_2O_3$ (molar ratio) and the adsorption amount of phosphate in the boehmite of the invention.

FIG. 3 also indicates the relationship between the ratio of SO$_4$/Al$_2$O$_3$ (molar ratio) and the adsorption amounts of phosphate ions. FIG. 3 is also indicative of a positive correlation between the respective adsorption amounts of sulfate ions and phosphate ions and a noticeably high correlation function of 0.956. Therefore the amount of phosphate ions to be adsorbed on the boehmite is controllable by varying the amount of sulfate ions.

TABLE 3

| Final mixture (pH) | (Not treated) | 5.0 | 4.0 | 3.0 | 1.9 |
|---|---|---|---|---|---|
| Amount of aqueous solution of sulfuric acid (ml) | — | 30 | 60 | 80 | 125 |
| Al$_2$O$_3$ (%) | 68.27 | 67.90 | 65.76 | 65.84 | 65.00 |

TABLE 3-continued

| Final mixture (pH) | (Not treated) | 5.0 | 4.0 | 3.0 | 1.9 |
|---|---|---|---|---|---|
| $SO_4$ (%) | 1.00*2 | 4.16 | 4.98 | 7.49 | 8.32 |
| Adsorption amount of phosphate ions (mg $PO_4$/g) | 25.12 | 43.97 | 54.28 | 60.45 | 65.16 |
| $SO_4/Al_2O_3$ (molar ratio) | 0.016 | 0.065 | 0.080 | 0.121 | 0.136 |
| 1:x:n*1 | 1:0.007:0.322 | 1:0.03:0.27 | 1:0.038:0.328 | 1:0.058:0.216 | 1:0.063:0.171 |

*1 $AlO(OH).xSO_4.nH_2O$
*2 The starting boehmite contains a small quantity of $SO_4$ as impurity.

We claim:

1. A boehmite-type aluminum hydroxide which is represented by the formula $$AlO(OH).xSO_4.nH_2O$$

wherein $0.01 < x < 0.10$ and $0 \leq n < 1$.

2. A boehmite-type aluminum hydroxide according to claim 1 wherein $0.03 \leq x < 0.10$.

3. A boehmite-type aluminum hydroxide according to claim 1 wherein $0.2 \leq n \leq 0.8$.

4. A process for preparing a boehmite-type aluminum hydroxide represented by the formula $$AlO(OH).xSO_4.nH_2O$$

wherein $0.01 < x < 0.10$ and $0 \leq n < 1$, the process comprising surface-treating a starting boehmite by bringing sulfuric acid or a sulfate into contact with the starting boehmite, said starting boehmite being a boehmite-type aluminum hydroxide represented by the formula $$AlO(OH).mH_2O$$

wherein $0 \leq m < 1$, and said sulfate being at least one compound selected from the group consisting of ammonium sulfate, ammonium hydrogensulfate, sodium hydrogensulfate and potassium hydrogensulfate.

5. A process according to claim 4 wherein the surface treatment is conducted by adding an aqueous solution of sulfuric acid or an aqueous solution of a sulfate to an aqueous suspension of a boehmite-type aluminum hydroxide represented by the formula $$AlO(OH).mH_2O$$

wherein $0 \leq m < 1$.

6. A process according to claim 5 wherein the aqueous solution is added to the suspension with stirring.

7. A process according to claim 4 wherein the sulfate is ammonium sulfate.

8. A process according to claim 4 wherein the sulfate is at least one member selected from the group consisting of ammonium hydrogensulfate, sodium hydrogensulfate and potassium hydrogensulfate.

9. A phosphate ion-absorbing composition containing as its effective component a boehmite-type aluminum hydroxide represented by the formula $$AlO(OH).xSO_4.nH_2O$$

wherein $0.01 < x < 0.10$ and $0 \leq n < 1$, and, when required, a diluent or an excipient.

10. A phosphate ion-absorbing composition according to claim 9 including a pharmaceutically acceptable, diluent or excipient.

11. A phosphate ion-absorbing composition according to claim 9 wherein $0.03 \leq x < 0.10$.

12. A phosphate ion-absorbing composition according to claim 9 wherein $0.2 \leq n \leq 0.8$.

13. A phosphate ion-absorbing composition according to claim 9 which is provided as a preparation in the form of granules or tablets.

14. A phosphate ion-absorbing composition according to claim 9 suitable for administration at a daily dose of about 3 to about 6 g per adult.

* * * * *